United States Patent [19]

Danz et al.

[11] Patent Number: 4,568,427
[45] Date of Patent: Feb. 4, 1986

[54] CONTINUOUS ISOLATION OF PHTHALIC ANHYDRIDE AND MALEIC ANHYDRIDE FROM REACTION GASES

[75] Inventors: Eckehard Danz, Ludwigshafen; Gerd Dümbgen, Dannstadt-Schauernheim; Ernest Miesen, Ludwigshafen; Johannes E. Schmidt, Ludwigshafen; Friedrich Wirth, Ludwigshafen, all of Fed. Rep. of Germany

[73] Assignee: BASF Aktiengesellschaft, Fed. Rep. of Germany

[21] Appl. No.: 465,767

[22] Filed: Feb. 11, 1983

[30] Foreign Application Priority Data

Feb. 27, 1982 [DE] Fed. Rep. of Germany ....... 3207208

[51] Int. Cl.[4] .............................................. B01D 3/34
[52] U.S. Cl. ........................................ 203/57; 203/14; 203/42; 203/71; 203/74; 549/250
[58] Field of Search .................. 203/61, 71, 74, 57, 203/42, 14, 3; 549/247, 248, 249, 250

[56] References Cited

U.S. PATENT DOCUMENTS

| | | | |
|---|---|---|---|
| 2,140,140 | 12/1938 | Punnett | 549/250 |
| 2,683,110 | 7/1954 | Rousseau | 549/250 |
| 2,770,630 | 11/1956 | Miller | 549/250 |
| 2,893,924 | 7/1959 | Courtier | 549/250 |
| 2,942,005 | 6/1960 | Brown et al. | 260/346.4 |
| 3,040,060 | 6/1962 | Kulik | 549/250 |
| 4,008,255 | 2/1977 | Wirth et al. | 549/250 |
| 4,071,540 | 1/1978 | Marquis | 549/250 |
| 4,285,871 | 8/1981 | Keunecke et al. | 549/250 |

FOREIGN PATENT DOCUMENTS

| | | | |
|---|---|---|---|
| 2313306 | 9/1974 | Fed. Rep. of Germany . | |
| 654469 | 6/1951 | United Kingdom | 549/250 |
| 833230 | 4/1960 | United Kingdom | 549/248 |
| 832619 | 4/1960 | United Kingdom . | |
| 1130393 | 10/1968 | United Kingdom | 549/250 |

OTHER PUBLICATIONS

Norman, W. S., *Absorption, Distillation and Cooling Towers*, John Wiley & Sons Inc., N.Y., 1961, pp. 80-81.

Primary Examiner—S. Leon Bashore
Assistant Examiner—V. Manoharan
Attorney, Agent, or Firm—Keil & Weinkauf

[57] ABSTRACT

A process for the continuous isolation of phthalic anhydride and maleic anhydride from the reaction gases obtained by catalytic oxidation of o-xylene or naphthalene with air, wherein the reaction gases are treated with a hydrocarbon of boiling range from 115° to 175° C. as the solvent in a column, and are then treated with an organic solvent of boiling range from 180° to 290° C. in a second column, the phthalic anhydride and maleic anhydride being isolated from the liquid bottom product of the first column.

5 Claims, 1 Drawing Figure

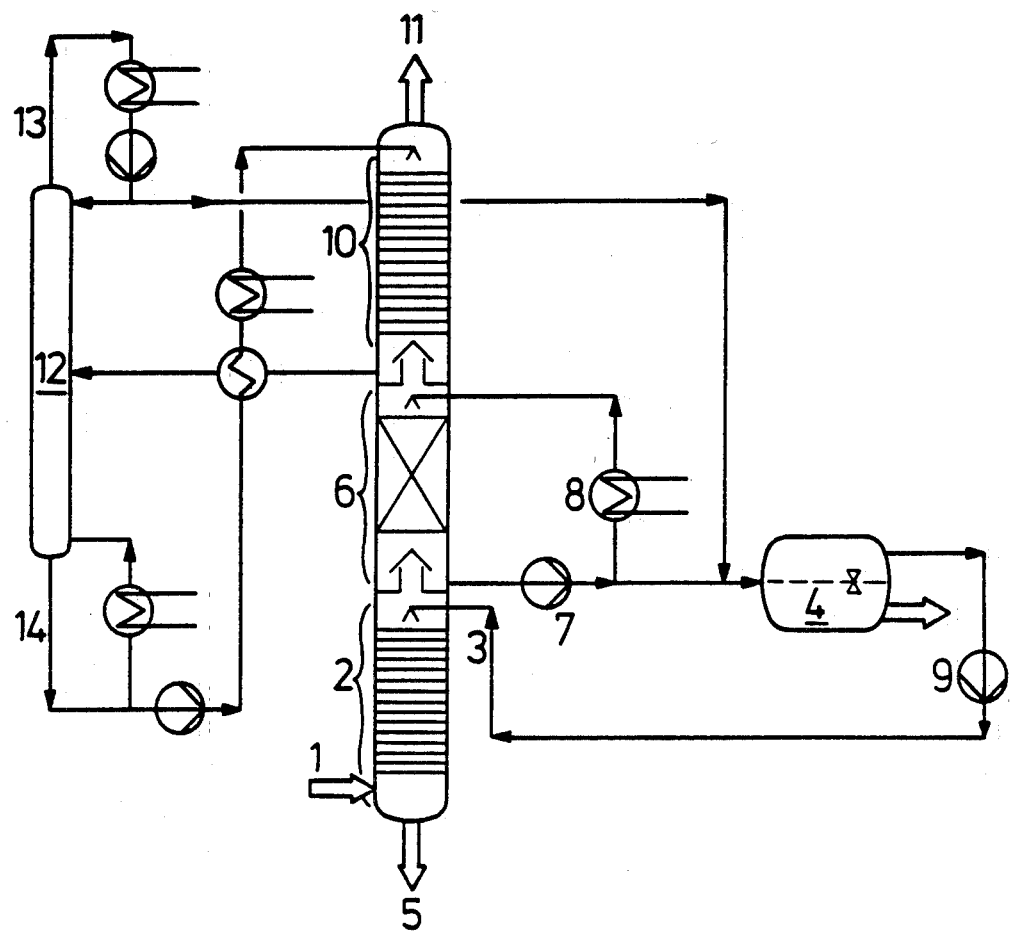

CONTINUOUS ISOLATION OF PHTHALIC ANHYDRIDE AND MALEIC ANHYDRIDE FROM REACTION GASES

The present invention relates to a novel continuous process for isolating phthalic anhydride and maleic anhydride from reaction gases obtained by catalytic oxidation of o-xylene or naphthalene with air.

Phthalic anhydride is produced industrially by catalytic oxidation of o-xylene or naphthalene with air. The reaction gases obtained by such oxidation contain, for example, 80 g/m$^3$ (S.T.P.) of phthalic anhydride, 5 g/m$^3$ (S.T.P.) of maleic anhydride and 60 g/m$^3$ (S.T.P.) of water vapor and after heat recuperation are still at about 180° C. The phthalic anhydride is separated out from the reaction gases by desublimation on heat-transfer surfaces. For this, large, finned tube condensers are used, on which, during the charging phase, the phthalic anhydride desublimes as a result of the cooling of the tubes, and is subsequently melted off by periodically heating the tubes. The crude phthalic anhydride is finally freed from by-products in a purification stage, preferably by distillation. Since an industrial plant requires the installation of a plurality of such desublimators, the isolation of the phthalic anhydride from the reaction gases entails great expense in respect of investment, repairs and energy consumption. Moreover, the periodic cooling and heating prevent continuous operation.

The maleic anhydride also present in the reaction gases separates out only partially in the desublimators. To isolate the maleic anhydride it is therefore necessary to subject the reaction gases to a subsequent water wash. The aqueous maleic acid solution thus obtained then has to be subjected to a process which is again energy-intensive, namely evaporation and dehydration of the acid to the anhydride. The process requires high temperatures and expensive corrosion-resistant materials of construction. Finally, the maleic anhydride is purified by distillation.

To simplify this expensive technology, attempts have been made to isolate the anhydrides by washing the reaction gases with solvents. For example, U.S. Pat. No. 2,942,005 describes a process wherein a wash is effected with dibutyl phthalate or dipropyl phthalate as the solvent. The absorbed maleic anhydride is distilled off, and the phthalic anhydride is crystallized out by cooling the residue, and is isolated mechanically. The solvent is recycled to the gas wash, while the phthalic anhydride must be subjected to a plurality of further purification stages in order first to remove residual solvent and then to remove other impurities.

In the process of British Pat. No. 832,619, the reaction gas is washed with hydrocarbons which boil above 200° C., such as tetradecane or pentadecane. After a preliminary removal of the maleic anhydride, by distillation, the phthalic anhydride is isolated by azeotropic distillation. However, the azeotropes formed consist predominantly of the hydrocarbons. The phthalic anhydride is separated out of these mixtures by phase separation. It has a residual hydrocarbon content of from 4 to 5% by weight, which must be removed by distillation.

German Laid-Open Application DOS No. 2,313,306 describes a gas wash employing C$_{26-44}$-paraffins. In this method, the phthalic anhydride is isolated from the slurry by crystallization and mechanical separation. However, residual solvent must once again be removed by distillation.

These conventional processes all have the disadvantage that the purification of the phthalic anhydride to remove residues of the solvent used is involved and requires special measures.

Finally, it has been proposed to isolate phthalic anhydride and maleic anhydride by treating the reaction gases with a mixture of these anhydrides (German Laid-Open Applications DOS No. 2,855,629 and DOS No. 2,855,630). In these multi-stage absorption processes, complete isolation of the maleic anhydride requires subjecting the exit gas to a water wash. This means that once again the disadvantages, mentioned above, of isolating maleic anhydride from an aqueous maleic acid solution have to be accepted.

We have found that in the continuous isolation of phthalic anhydride and maleic anhydride from the reaction gases obtained by catalytic oxidation of o-xylene or naphthalene with air, by treating the reaction gases with a solvent, the disadvantages mentioned are avoided if (a) the reaction gases, at a temperature of above 135° C., are introduced into the lower zone of a column, and an organic water-immiscible solvent of boiling range from 115° to 175° C. is introduced into the upper zone of the column, (b) to recover residual solvent, the reaction gases leaving the top of the column are treated with a second organic solvent, which has a boiling range of from 180° to 290° C. and is miscible with the first solvent, in counter-current in a second column, and (c) the bottom product from the first column, which essentially consists of phthalic anhydride and maleic anhydride, is taken off as liquid.

Using the novel process, the two anhydrides are obtained in a particularly advantageous manner conjointly in the form of a liquid mixture which is substantially free from the solvents used. Moreover, any significant absorption of the water vapor contained in the reaction gases is avoided.

The process according to the invention is suitable for all reaction gases obtained by the conventional catalytic oxidation of o-xylene or naphthalene with air. These reaction gases contain, for example, from 35 to 100 g/m$^3$ (S.T.P.) of phthalic anhydride and from 1 to 5 g/m$^3$ (S.T.P.) of maleic anhydride.

According to the process of the invention, the reaction gases are passed into the lower zone of a column at above 135° C., for example at from 135° to 200° C., preferably from 150° to 180° C. Examples of suitable columns are tray columns with from 10 to 20 trays.

The solvent is introduced into the upper zone of the column. The solvents used according to the invention are hydrocarbons which boil at from 115° to 175° C., preferably from 135° to 155° C., and are water-immiscible, i.e. do not dissolve more than 1% of water at room temperature. Examples of suitable solvents of the stated type are the xylenes (meta-, ortho- or para-xylene), ethylbenzene, n-nonane and iso-nonane. In this process, the solvents mentioned have the great advantage that the absorption of the anhydrides from the reaction gas, which takes place in the column, does not require additional energy. Thus, the solvent is present on the upper trays of the column while at the bottom of the column a liquid mixture of the anhydrides separates out, whose composition corresponds to the ratio of the components in the reaction gas, and which does not contain significant amounts of the solvents. The liquid mixture, which consists, for example, of 94% by weight of phthalic anhydride and 5% by weight of maleic anhydride, is taken from the bottom of the column and separated into the pure anhydrides by distillation in a conventional manner.

Though, in this process, relatively low temperatures occur in the absorption column and water vapor is present, surprisingly no solid phthalic anhydride, phthalic acid or maleic acid separates out, and accordingly completely continuous operation is feasible.

The resultant gases saturated with solvent, which leave the top of the column are subjected to solvent recovery in a second column, using the second solvent. In a particularly advantageous embodiment of the invention, the resultant gases are cooled after leaving the first column, to from 40° to 20° C. depending on what is technically feasible under the given circumstances. This cooling causes condensation of a substantial part of the organic solvent present in the resultant gases, as well as of the water of reaction. Advantageously, the gases are cooled in a quenching chamber. The water is discharged from the system via a phase separation vessel. An appropriate amount of the solvent is charged, as reflux, onto the top tray of the absorption column. Since the resultant gases still contain substantial amounts of solvent and water vapor after they have been cooled, they are subjected to solvent recovery by being treated, in counter-current, with an organic solvent which boils at from 180° to 290° C., preferably from 220° to 240° C., and is miscible with the solvent to be absorbed. This treatment is advantageously carried out in a tray column, having from 10 to 20 trays. Examples of suitable second solvents of the stated type are hydrocarbons, e.g. diphenyl, aromatic ethers, e.g. diphenyl oxide, or carboxylic acids, e.g. isononanoic acids or ethylhexanoic acid. Particularly suitable solvents are carboxylic acids, such as ethylhexanoic acid, which, for example if o-xylene is used as the first solvent, and a column of from 10 to 20 trays is employed, permits virtually quantitative absorption. In the absorption using the high-boiling solvent, small amounts of water are also absorbed. The mixture of the two solvents, also containing water, which is obtained at the bottom of the absorption column is advantageously separated in a distillation column.

The top product from the distillation column, which contains the more volatile solvent and water, is charged into the separating vessel referred to above. The high-boiling organic solvent is obtained at the bottom of the distillation column, which can, where appropriate, be operated under suitably reduced pressure, and this solvent is advantageously passed to the top of the absorption column. Small amounts of contaminated solvent can, if necessary, be discharged from the system and replaced by fresh solvent.

A more detailed description of the invention follows in the example presented below of a preferred embodiment. For a better understanding, reference should be made to the accompanying drawing which illustrates diagrammatically a typical apparatus which may be employed in carrying out the process and is described in the example.

EXAMPLE

The process gas, which is obtained by catalytic oxidation of o-xylene with air, is at 180° C. and is laden with 80 g/m³ (S.T.P.) of phthalic anhydride, 5 g/m³ (S.T.P.) of maleic anhydride and 60 g/m³ (S.T.P.) of water vapor, is introduced, in the manner illustrated in the FIGURE, from below (1) into an adiabatically operated column having 17 trays (2). At the top of the column (3), o-xylene at 30° C. is introduced from the separating vessel (4). The amount is regulated so that neither does a significant amount of o-xylene leave the bottom of the column (2) nor is a significant amount of phthalic anhydride or maleic anhydride discharged with the gas from the column. A temperature profile becomes established in the adiabatically operated column, and is employed to regulate the amount of o-xylene.

The temperature is 142° C. at the bottom, decreasing to 70° C. at the top, i.e. 17th, tray. This is not so low as to cause condensation of the water vapor (dew point about 40° C.). The liquid mixture of phthalic anhydride and maleic anhydride leaving the bottom of column (5) has a residual content of less than 0.01% by weight of o-xylene and of about 0.5% by weight of the two acids. It is subsequently separated by distillation. The gas which passes from the top of the column (2) into the quenching chamber (6) is cooled to 30° C. The quenching system also includes a pump (7), and a heat exchanger (8) operated with cooling water. The liquid mixture of o-xylene and water, obtained in the quenching chamber (6), is separated in the separating vessel (4). The upper phase, consisting of o-xylene, is returned via a pump (9) to the top of the column (3). Per m³ (S.T.P.) of reaction gas, 0.43 kg of o-xylene is required. The water from the separating vessel (4), which can, if desired, be freed from residual o-xylene by stripping, contains only small amounts of phthalic anhydride and maleic anhydride lost from the column (2). The total amount is about 0.1% of the joint yield of phthalic anhydride and maleic anhydride. After the quenching chamber (6), the gas, at 30° C., passes through an absorption column (10), above the quenching chamber, in which the gas is treated with ethylhexanoic acid in order to absorb residual solvent. This column has 15 trays, which, using 0.24 kg of the ethylhexanoic acid wash liquid per m³ (S.T.P.) of gas, suffices to reduce the losses of o-xylene at the top of the absorption column to a mere 0.05 g/m³ (S.T.P.). The exit gas (11) moreover contains, at 30° C., 0.1 g/m³ (S.T.P.) of residual ethylhexanoic acid. At the bottom of the absorption column (10), a mixture of 80.4% by weight of ethylhexanoic acid, 19.0% by weight of o-xylene and 0.6% by weight of water is obtained. This mixture is passed to the distillation column (12) where o-xylene and water are obtained as the top product (13), which is passed into the separating vessel (4). The ethylhexanoic acid bottom product (14) is cooled to 30° C. and recycled to the top of the absorber column (10). The distillation (12) can be operated under atmospheric pressure but is preferably run under 130 mbar. A part-stream of the ethylhexanoic acid (2–3%) is taken off and purified by distillation.

We claim:

1. A continuous process for the separation of phthalic anhydride and maleic anhydride from the hydrous reaction gas mixture formed during the production of said anhydride by the catalytic air-oxidation of o-xylene or naphthalene which comprises:

(a) introducing said reaction gas mixture at a temperature of from 135° to 200° C. into the lower zone of a first adiabatically operated column and a first solvent consisting of a water-immiscible hydrocarbon having a boiling point in the range of from about 115° to 175° C. into the upper zone of said column, (b) effecting contact of said reaction gas mixture with said hydrocarbon solvent in the upper zone of said first column to separate said anhydride from the reaction gas mixture, the amount of said hydrocarbon solvent introduced into said first column being regulated so that neither a significant amount of solvent leaves the bottom of the column, nor a significant amount of anhydride is discharged from the column as a gas, (c) causing the resultant gas mixture laden with the residual hydrocarbon solvent to exit said first column at the top thereof and to enter a second column at the bottom thereof, (d) introducing a second hydrocarbon-containing solvent miscible with said first solvent and having a boiling point in the range of from 180° to 290° C. into the upper zone of said second column to effect a counter-current flow with said first residual solvent in order to absorb said residual solvent, (e) passing the resulting mixture of said first and second solvents to a distillation column to effect separation followed by a recycling of the separated solvents for re-use in said process; and (f) continuously removing phthalic anhydride and maleic anhydride in liquid form as bottom product from said first column.

2. The process in accordance with claim 1, wherein the resultant gas mixture exiting the top of said first column is cooled to a temperature in the range of from about 40° to 20° C. before entering the bottom of said second column.

3. The process in accordance with claim 1, wherein the recovered first solvent is passed to a separation vessel to remove water therefrom before recycling for further use in the process.

4. The process in accordance with claim 1, wherein o-xylene is used as said first solvent.

5. The process in accordance with claim 1, wherein ethylhexanoic acid is used as said second solvent.

* * * * *